(12) United States Patent
Gellman et al.

(10) Patent No.: US 10,463,688 B2
(45) Date of Patent: Nov. 5, 2019

(54) NYLON-3 POLYMERS ACTIVE AGAINST CLOSTRIDIUM DIFFICILE

(71) Applicants: Wisconsin Alumni Research Foundation, Madison, WI (US); Emory University, Atlanta, GA (US)

(72) Inventors: Samuel H. Gellman, Madison, WI (US); Runhui Liu, Madison, WI (US); Bernard Weisblum, Madison, WI (US); Shonna M. McBride, Atlanta, GA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/198,588

(22) Filed: Jun. 30, 2016

(65) Prior Publication Data

US 2017/0000818 A1 Jan. 5, 2017

Related U.S. Application Data

(60) Provisional application No. 62/187,872, filed on Jul. 2, 2015.

(51) Int. Cl.
*A61K 31/787* (2006.01)
*A61K 31/785* (2006.01)

(52) U.S. Cl.
CPC .................................. *A61K 31/787* (2013.01)

(58) Field of Classification Search
None
See application file for complete search history.

(56) References Cited

U.S. PATENT DOCUMENTS

| 8,519,085 B2 | 8/2013 | Stahl et al. | |
| 2008/0076716 A1* | 3/2008 | Zhang | C07K 14/4723 514/2.4 |
| 2015/0231171 A1* | 8/2015 | Gellman | A61K 31/785 424/78.3 |

FOREIGN PATENT DOCUMENTS

WO WO-2011116188 A1 * 9/2011 ........... A61K 9/0082

OTHER PUBLICATIONS

Liu et al. "Synthetic Polymers Active against Clostridium difficile Vegetative Cell Growth and Spore Outgrowth" (Year: 2014).*
Allen et al., Both Fidaxomicin and Vancomycin Inhibit Outgrowth of *Clostridium difficile* Spores, *Antimicrob. Agents Chemother.* 2013, vol. 57, No. 1, 664-667.
Arzese et al., Antimicrobial activity of SMAP-29 against the *Bacteroides fragilis* group and clostridia, *Antimicrob. Chemother.* 2003, 52, 375-381.
Balaban et al., A problem of persistence: still more questions than answers? *Nat. Rev. Microbiol.* 2013, vol. 11, 587-591.
Bartlett et al., Antibiotic-Associated Pseudomembranous Colitis, *Rev. Infect. Dis.* 1979, vol. 1, No. 3, 530-539.
Boman et al., Antibacterial peptides: basic facts and emerging concepts, *J. Intern. Med.* 2003, 254, 197-215.
Bouillaut et al., Genetic Manipulation of *Clostridium difficile*. *Current Protocols in Microbiology*; John Wiley & Sons, Inc.: New York, 2011; Chapter 9, Unit 9A.2.
Chilton et al., Evaluation of the effect of oritavancin on Clostridium difficile spore germination, outgrowth and recovery, *J. Antimicrob. Chemother.* 2013, 68, 2078-2082.
Cornely et al., Treatment of First recurrence of *Clostridium difficile* Infection: Fidaxomicin Versus Vancomycin, *Clin. Infect. Dis.* 2012, 55 (Suppl 2), S154-S161.
Deakin et al., The *Clostridium difficile* spo0A Gene Is a Persistence and Transmission Factor, *Infect. Immun.* 2012, vol. 80, No. 8, 2704-2711.
Edwards et al., Culturing and Maintaining *Clostridium difficile* in an Anaerobic Environment, *J. Visualized Exp.* 2013, DOI: 10.3791/50787.
Edwards et al., Conserved Oligopeptide Permeases Modulate Sporulation Initiation in *Clostridium difficile*, *Infect. Immun.* 2014, vol. 82, No. 10, 4276-4291.
EUCAST (European Committee for Antimicrobial Susceptibility Testing), Determination of minimum inhibitory concentrations (MICs) of antibacterial agents by broth dilution, *European Society of Clinical Microbiology and Infectious Diseases*, 2003, 9, ix-xv.
Fisher et al., The dltABCD Operon of *Bacillus anthracis* Sterne Is Required for Virulence and Resistance to Peptide, Enzymatic, and Cellular Mediators of Innate Immunity, *J. Bacteriol.* 2006, vol. 188, No. 4, 1301-1309.
Frackenpohl et al., The Outstanding Biological Stability of β- and γ-Peptides toward Proteolytic Enzymes: An In Vitro Investigation with Fifteen Peptidases, *ChemBioChem* 2001, 2, 445-455.
Gerding et al., *Clostridium difficile*-Associated Diarrhea and Colitis, *Infect. Control Hosp. Epidemiol.* 1995, vol. 16, No. 8, 459-477.
Gut et al., Inhibition of *Bacillus Anthracis* Spore Outgrowth by Nisin, *Antimicrob. Agents Chemother.* 2008, vol. 52, No. 12, 4281-4288.
Hancock et al., Antimicrobial and host-defense peptides as new anti-infective therapeutic strategies, *Nature Biotechnol.* 2006, vol. 24, No. 12, 1551-1557.
Hedge et al., New advances in the treatment of *Clostridium difficile* infection (CDI), *Ther. Clin. Risk Manage.* 2008, 4(5), 949-964.
Hussain et al., Generation of an erythromycin-sensitive derivative of *Clostridium difficile* strain 630 (630Aerm) and demonstration that the conjugative transposon Tn916ΔE enters the genome of this strain at multiple sites, *J. Med. Microbiol.* 2005, 54, 137-141.
Kelly, C. P., Can we identify patients at high risk of recurrent *Clostridium difficile* infection?, Clin. *Microbial. Infect.* 2012, 18 (Suppl 6), 21-27.
Larson et al., Pseudomembranous Colitis: Presence of Clostridial Toxin, *Lancet* 1977, 2, 1312-1314.

(Continued)

*Primary Examiner* — Susan T Tran
(74) *Attorney, Agent, or Firm* — Joseph T. Leone, Esq.; DeWitt LLP (57) ABSTRACT

A method and corresponding composition to inhibit outgrowth of *C. difficile* spores and/or to inhibit growth of *C. difficile* vegetative cells in a mammal in which an amount of a nylon-3 polymer or nylon-3 copolymer or a pharmaceutically suitable salt thereof is administered to the subject.

16 Claims, 4 Drawing Sheets

(56) References Cited

OTHER PUBLICATIONS

Liu et al., Nylon-3 Polymers That Enable Selective Culture of Endothelial Cells, *J. Am. Chem. Soc.* 2013, 135, 16296-16299.
Liu et al., Nylon-3 Polymers with Selective Antifungal Activity, *J. Am. Chem. Soc.* 2013, 135, 5270-5273.
Liu et al., Tuning the Biological Activity Profile of Antibacterial Polymers via Subunit Substitution Pattern, *J. Am. Chem. Soc.* 2014, 136, 4410-4418.
Liu et al., Structure-Activity Relationships among Antifungal Nylon-3 Polymers: Identification of Materials Active against Drug-Resistant Strains of *Candida Albicans J. Am. Chem. Soc.* 2014, 136, 4333-4342.
Louie et al., Fidaxomicini versus Vancomycin for *Clostridium difficile* infection, *New Engl. J. Med.* 2011, 364, 422-431.
Mazzotta et al., Nisin Resistance in *Clostridium botulinum* Spores and Vegetative Cells, *J. Appl. Environ. Microbial.* 1997, 63, 2654-2659.
McBride et al., Identification of a Genetic Locus Responsible for Antimicrobial Peptide Resistance in *Clostridium difficile, Infect. Immun.* 2011, 79, 167-176.
McBride et al., the dlt operon confers resistance to cationic antimicrobial peptides in *Clostridium difficile, Microbiology* 2011, 157, 1457-1465.
Moir, A., How do spores germinate? *J. Appl. Microbial.* 2006, 101, 526-530.
Moir et al., The Genetics of Bacterial Spore Germination, *Annu. Rev. Microbial*, 1990, 44, 531-553.
Mueller et al., A Protein-Free Medium for Primary Isolation of the Gonococcus and Meningococcus, *J. Proc. Soc. Exp. Biol. Med.* 1941, 48, 330-333.
Mullane et al., Efficacy of Fidaxomicin Versus Vancomycin as Therapy for *Clostridium* difficile Infection in Individuals Taking Concomitant Antibiotics for Other Concurrent Infections, *Clin. Infect. Dis.* 2011, 53, 440-447.
Musher et al., Relatively Poor Outcome after Treatment of *Clostridium difficile* Colitis with Metronidazole,, *J. Clin. Infect. Dis.* 2005, 40, 1586-1590.
Paredes-Sabja et al., Germination of spores of *Bacillales* and *Clostridiales* species: mechanisms and proteins involved, *Trends Microbiol* 2011, vol. 19, No. 2, 85-94.
Paredes-Sabja et al., *Clostridium difficile* spore biology: sporulation, germination, and spore structural proteins, *Trends Microbiol.* 2014, vol. 22, No. 7, 406-416.
Petrella et al., Decreased Cure and Increased Recurrence Rates for *Clostridium difficile* Infection Caused by the Epidemic *C. difficile* BI Strain, *Clin. Infect. Dis.* 2012, 55, 351-357.
Putnam et al., SpoIVA and sipL are *Clostridium difficile* Spore Morphogenetic, *J. Bacteriol.* 2013, vol. 195, 1214-1225.
Raguse et al., Structure-Activity Studies of 14-Helical Antimicrobial β-Peptides: Probing the Relationship between Conformational Stability and Antimicrobial Potency, *J. Am. Chem. Soc.* 2002, 124, 12774-12785.
Rupnik et al., *Clostridium difficile* infection: new developments in epidemiology and pathiogenesis, *Nat. Rev. Microbiol.* 2009, vol. 7, 526-536.
Scott et al., Temperature, pH, and Spore Load Effects on the Ability of Nisin to Prevent the Outgrowth of *Clostridium botulinum* spores, *J. Food Sci.* 1981, vol. 46, 121-126.
Setlow, P., Spore germination, *Curr. Opin. Microbiol.* 2003, 6, 550-556.
Setlow, P. Summer meeting 2013—when the sleepers wake: the germination of spores of *Bacillus* species, *J. Appl. Microbiol.* 2013, 115, 1251-1268.
Smith et al., Transferable Tetracycline Resistance in *Clostridium difficile, Antimicrob. Agents Chemother.* 1981, vol. 19, No. 6, 997-1003.
Sorg et al., Bile Salts and Glycine as Cogerminants for *Clostridium difficile* Spores *J. Bacteriol.* 2008, vol. 190, No. 7, 2505-2512.
Sorg et al., Laboratory Maintenance of *Clostridium difficile. Current Protocols in Microbiology*; John Wiley & Sons, Inc.: New York, 2009; Chapter 9, Unit 9A.1.
Sorg et al., Inhibiting the Initiation of *Clostridium difficile* Spore Germination using Analogs of Chenodeoxycholic Acid, a Bile Acid, *J. Bacteriol.* 2010, vol. 192, No. 19, 4983-4990.
Stabler et al., Comparative genome and phenotypic analysis of *Clostridium difficile* 027 strains provides insight into the evolution of a hypervirulent bacterium, *Genome Biol.* 2009, vol. 10, Issue 9, R102-R102-15.
Suarez et al., the *Clostridium difficile* cpr Locus Is Regulated by a Noncontiguous Two-Component System in Response to type A and B Lantibiotics, *J. Bacteriol.* 2013, vol. 195, No. 11, 2621-2631.
Vonberg et al., costs of nosocomial *Clostridium difficile*-associated diarrhea, *Journal of Hospital Infection*, 2008, 70, 15-20.
Wilson et al., role of competition for Nutrients in Suppression of *Clostridium difficile* by the Colonic Microflora, *Infect. Immun.* 1988, vol. 56, No. 10, 2610-2614.
Wüst et al., Transferable Resistance to Clindamycin, Erythromycin, and Tetracycline in *Clostridium difficile, Antimicrob. Agents Chemother.* 1983, vol. 23, No. 5, 784-786.
Zar et al., A comparison of Vancomycin and Metronidazole for the Treatment of *clostridium difficile*—Associated Diarrhea, Stratified by disease Severity, *Clin. Infect. Dis.* 2007, 45, 302-307.
Zasloff, M., Antimicrobial peptides of multicellular organisms, *Nature* 2002, vol. 415, 389-395.

* cited by examiner

NYLON-3 POLYMERS ACTIVE AGAINST *CLOSTRIDIUM DIFFICILE*

CROSS-REFERENCE TO RELATED APPLICATIONS

Priority is hereby claimed to provisional application Ser. No. 62/187,872, filed Jul. 2, 2015, which is incorporated herein by reference.

FEDERAL FUNDING STATEMENT

This invention was made with government support under EB013529, AI092225, and GM093265 awarded by the National Institutes of Health and 0832760 awarded by the National Science Foundation. The government has certain rights in the invention.

BACKGROUND

*Clostridium difficile* is a Gram-positive, endospore-forming anaerobe that causes life-threatening intestinal infections. *C. difficile* infections, or CDIs, lead to billions of dollars in healthcare costs and result in over 14,000 deaths per year in the United States alone. *C. difficile* has been listed by the U.S. Centers for Disease Control and Prevention (CDC) as the highest level threat of antibiotic resistance in the United States. (Office of the Associate Director for Communication, Digital Media Branch, Division of Public Affairs. Antibiotic Resistance Threats in the United States, 2013; Centers for Disease Control and Prevention: Atlanta, Ga., Sep. 16, 2013; http://www.cdc.gov/features/AntibioticResistanceThreats/.) Because *C. difficile* is a strict anaerobe, the bacterium can survive outside of the host intestine only as a dormant spore. For *C. difficile* to cause disease, the spores must be ingested. The spores germinate when exposed to bile salts in the intestine, yielding the vegetative form of the bacterium. Once in the vegetative form, *C. difficile* can produce the toxins that are responsible for disease manifestations. See, for example, Deakin, L. J., et al. *Infect. Immun.* 2012, 80, 2704; Sorg, J. A.; Sonenshein, A. L. *J. Bacteriol.* 2008, 190, 2505; Larson, H. E.; Price, A. B. *Lancet* 1977, 2, 1312; and Bartlett, J. G. *Rev. Infect. Dis.* 1979, 1, 530.

*C. difficile* infections are often preceded by the use of therapeutic antibiotics to treat unrelated bacterial infections. (Rupnik, M.; Wilcox, M. H.; Gerding, D. N. *Nat. Rev. Microbiol.* 2009, 7, 526.) Antibiotic use disrupts the indigenous microbiota, allowing *C. difficile* to colonize and proliferate within the intestine. Current treatment of CDI typically consists of metronidazole, vancomycin, or, most recently, fidaxomicin. Unfortunately, these antibiotics are not able to treat all CDIs, and recurrence of disease occurs in many patients, especially when infections involve the epidemic 027 isolates. To combat this challenge, new strategies are being explored for the treatment of CDI. See Wilson, K. H.; Perini, F. *Infect. Immun.* 1988, 56, 2610; Kelly, C. P. *Clin. Microbiol. Infect.* 2012, 18 (Suppl 6), 21; Cornely, O. A.; Miller, M. A., et al. *Clin. Infect. Dis.* 2012, 55 (Suppl 2), S 154; Mullane, K. M., et al. *Clin. Infect. Dis.* 2011, 53, 440; Louie, T. J., et al. *New Engl. J. Med.* 2011, 364, 422; and Hedge, D. D., et al. *Ther. Clin. Risk Manage.* 2008, 4, 949.

Host-defense peptides (HDPs) have demonstrated potent activity against pathogenic bacteria and are considered promising candidates for the treatment of bacterial infections. Indeed, the human HDP LL-37 is a potent inhibitor of *C. difficile* growth. See Zasloff, M. *Nature* 2002, 415, 389; Boman, H. G. *J. Intern. Med.* 2003, 254, 197; Hancock, R. E.; Sahl, H. G. *Nature Biotechnol.* 2006, 24, 1551; McBride, S. M.; Sonenshein, A. L. *Infect. Immun.* 2011, 79, 167; and Arzese, A., et al. *Antimicrob. Chemother.* 2003, 52, 375. However, stepwise solid-phase synthesis of peptides is expensive. Synthetic polymers that can mimic the antimicrobial properties of HDPs are attractive because their production should be more facile than that of sequence-specific peptides, and the polymers resist proteolytic degradation. Although a variety of synthetic polymers have recently been examined for inhibition of bacterial growth, there is a long-felt and unmet need for synthetic polymers that inhibit the growth of *C. difficile* in general and for synthetic polymers that inhibit pathogenic spore outgrowth of *C. difficile* in particular.

SUMMARY

Disclosed herein a method, and a corresponding pharmaceutical composition, to inhibit the outgrowth of *C. difficile* spores and/or to inhibit the growth of *C. difficile* vegetative cells using nylon-3 copolymers as an active agent outgrowth/growth inhibitor.

Thus, disclosed herein is a pharmaceutical composition comprising an amount of a nylon-3 polymer or nylon-3 copolymer or a pharmaceutically suitable salt thereof, wherein the amount is effective to inhibit outgrowth of *C. difficile* spores and/or to inhibit growth of *C. difficile* vegetative cells. The composition may optionally comprise a pharmaceutically suitable delivery vehicle. The delivery vehicle may be suitable for enteral or parenteral administration.

The nylon-3 polymer or copolymer may optionally comprise subunits selected from the group consisting of wherein:

$R^3$, $R^4$, $R^5$, and $R^6$ are each independently selected from the group consisting of hydrogen, substituted or unsubstituted $C_1$-$C_6$-alkyl, aryl, $C_1$-$C_6$-alklyaryl, amino, protected-amino, amino-$C_1$-$C_6$-alkyl, protected-amino-$C_1$-$C_6$-alkyl, guanidine, thioalkyl, alkylthioalkyl, amino-substituted alkylthioalkyl, or $R^3$ and $R^4$ combined define a cyclic substituent selected from the group consisting of $C_4$-$C_{12}$ cycloalkyl, $C_4$-$C_{12}$ cycloalkenyl, and five- to twelve-membered heterocyclic;

"n" is an integer from 0 to 8; and

"A" is selected from the group consisting of substituted or unsubstituted $C_4$-$C_{12}$ cycloalkyl, $C_4$-$C_{12}$ cycloalkenyl, and five- to twelve-membered heterocyclic.

The pharmaceutical composition may include a nylon-3 polymer or copolymer that has at least 5 subunits, 10 subunits, at least 15 subunits, at least 20 subunits, or between 5 and 120 subunits. The nylon-3 polymer or copolymer may optionally be selected from the group consisting of:

NM:CH, x = 0.4-1, y = 1-x

MM:TM, R = H DM:TM, R = Me x = 0.4-1, y = 1-x

50:50 MM:CH

50:50 DM:CH

50:50 DM:TM

The nylon-3 polymer or copolymer may optionally be selected from the group consisting of:

and

R is selected from the same group of substituents as $R^3$ through $R^6$.

Also disclosed herein is a method of inhibiting outgrowth of *C. difficile* spores and/or inhibiting growth of *C. difficile* vegetative cells comprising contacting the spores or cells with an amount of a nylon-3 polymer or nylon-3 copolymer or a pharmaceutically suitable salt thereof, wherein the amount is effective to inhibit outgrowth of the *C. difficile* spores and/or to inhibit growth of the *C. difficile* vegetative cells. The nylon-3 polymers and/or copolymers may be the same as those disclosed in the immediately preceding paragraphs.

Also disclosed herein is a method of inhibiting outgrowth of *C. difficile* spores and/or inhibiting growth of *C. difficile* vegetative cells in a mammal, including a human. The method comprises administering to the mammal an amount of a nylon-3 polymer or nylon-3 copolymer or a pharmaceutically suitable salt thereof, wherein the amount is effective to inhibit outgrowth of the *C. difficile* spores and/or to inhibit growth of the *C. difficile* vegetative cells in the mammal. The nylon-3 polymers and/or copolymers may be the same as those disclosed in the immediately preceding paragraphs. The amount of the nylon-3 polymer or copolymer may be administered enterally or parenterally.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. The indefinite articles "a" and "an" mean "one or more" unless explicitly stated to the contrary.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry, microbiology, and/or pharmacy.

BRIEF DESCRIPTION OF THE DRAWINGS

FIG. 1A depicts photomicrographs of purified *C. difficile* spores from strain 630. FIG. 1B depicts photomicrographs of purified *C. difficile* spores from strain R20291. In both figures, the spores were incubated in MH broth supplemented with 5 mM taurocholate (TA) germinant and antimicrobial compounds as indicated. Samples were taken for phase-contrast microscopy at 15 min intervals over 1 h as described in the Detailed Description.

DETAILED DESCRIPTION

1. Abbreviations and Definitions

The following abbreviations and definitions are used. Terms not defined are to be given their accepted meaning within the field of chemistry or microbiology.

BHIS=Brain heart infusion-supplemented medium; for example, ATCC medium 1293. CDI=*C. difficile* infection. CFU=Colony-forming units. CH=cyclohexyl. DM=dimethyl. DMAc=dimethylacetamide. GPC=Gel permeation chromatography. HDP=Host-defense peptide. MH broth=Mueller Hinton broth. MIC=Minimum inhibitory concentration. MM=mono-methyl. NM=amino-methyl. OIC=Minimum inhibition concentration for spore outgrowth. TA=taurocholate. TFA=Trifluoroacetic acid. THF=tetrahydrofuran. TM=tetra-methyl.

"Pharmaceutically-suitable salt"=any acid or base addition salt whose counter-ions are non-toxic to the patient in pharmaceutical doses of the salts, so that the beneficial inhibitory effects inherent in the free base or free acid are not vitiated by side effects ascribable to the counter-ions. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N-methylmorpholine, and the like.

A "protecting group" is any chemical moiety capable of selective addition to and removal from a reactive site to allow manipulation of a chemical entity at sites other than the reactive site. A host of protecting groups are known in the art. An illustrative, non-limiting list of protecting groups includes methyl, formyl, ethyl, acetyl, t-butyl, anisyl, benzyl, trifluoroacetyl, N-hydroxysuccinimide, t-butoxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulphenyl, 4-toluenesulphonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, and 2,2,5,7,8-pentamethyl-chroman-6-sulphonyl. The term "protecting group" explicitly includes, without limitation t-butoxycarbonyl (tBOC), benzyloxycarbonyl (Cbz), benzyl (Bn), and allyloxycarbonyl (alloc). A "protected amine" is an amine moiety protected by a "protecting group." A host of suitable amine-protecting groups are known in the art. See, for example, Peter G. M. Wuts, "Greene's Protective Groups in Organic Synthesis, Fifth Edition,"© 2104, John Wiley & Sons, Inc., Hoboken, N.J. (ISBN 978-1118057483).

2. Nylon-3 Polymers

All copolymers tested were prepared in via anionic ring-opening copolymerization of a mixture of two β-lactam monomers. This method is disclosed in U.S. Pat. No. 8,519,085, Aug. 27, 2013, to Stahl et al., which is incorporated herein by reference. Polymers are named based on the β-lactam portion used for the polymerization reaction, as shown in Scheme 1. Thus, "50:50 DM:TM" is the copolymer produced from copolymerization of β-lactams DMβ and TMβ in 50:50 (mol:mol) ratio. The actual ratio of two subunits within each polymer can vary from the β-lactam proportion, especially for some of the MM:TM copolymers described below (see Table 2).

Scheme 1 nylon-3 polymers

Scheme 1 depicts the β-lactam monomers and the resulting nylon-3 copolymers actually fabricated and tested in the working examples. β-Lactams βNMP, MMβ and DIM gave the corresponding cationic, amine subunits within copolymers; β-lactams CHβ and TMβ gave the corresponding hydrophobic subunits.

Note that the various substitution patterns on the β-lactam monomers are exemplary only. Any substitution pattern, or any of the substitution patterns as disclosed in U.S. Pat. No. 8,519,085 may be used to fabricate suitable nylon-3 polymers for use herein. Nylon-3 homopolymers and/or copolymers of any description (random, block, etc.) may be used.

3. Nylon-3 Polymers Are Active Against *C. difficile* Vegetative Cells

Figure 3:
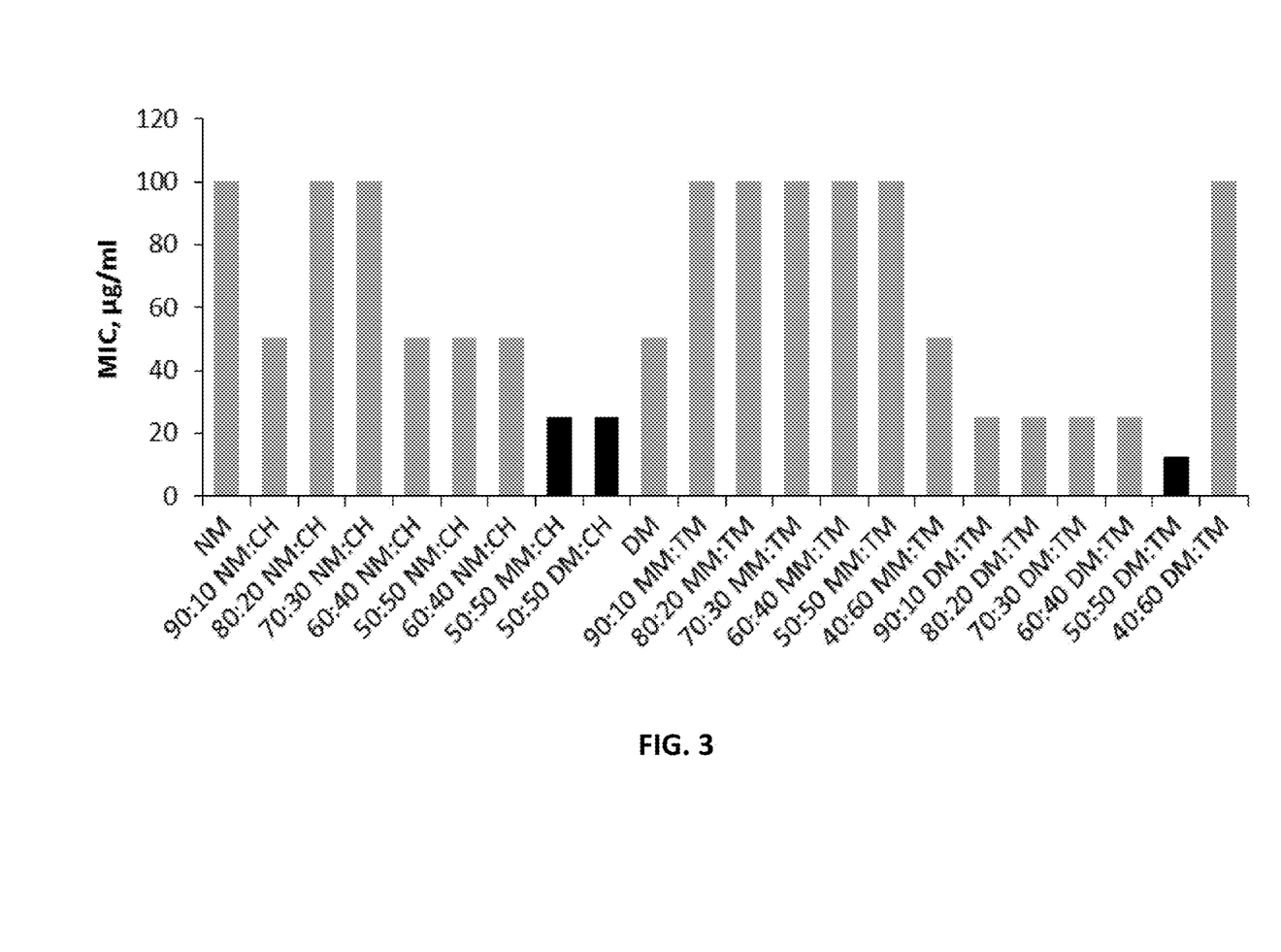
FIG. 3 is a histogram depicting the initial screening of various nylon-3 polymers against *C. difficile* vegetative cells (R20291 strain). Three of the most active co-polymers (50:50 MM:CH, 50:50 DM:CH, and 50:50 DM:TM; shown as the black bars) were selected for further study. See Scheme 1 for definitions.

In preliminary studies, a set of twenty-two (22) nylon-3 cationic homopolymers and binary hydrophobic-cationic copolymers was evaluated for the ability to inhibit growth of vegetative *C. difficile* (strain R20291; taxon identifier 645463). (See FIG. 3 and the examples below). All nylon-3 polymers were active against R20291 vegetative cells, with a minimum inhibitory concentration (MIC) range of 12.5 to 100 μg/mL. Among copolymers containing the cyclohexyl ("CH") hydrophobic unit, 50:50 MM:CH and 50:50 DM:CH displayed the lowest MIC values, while among copolymers containing the tetra-methyl ("TM") hydrophobic unit, 50:50 DM:TM displayed the lowest MIC value. These three copolymers (see Scheme 1) were selected for further study with two *C. difficile* strains, R20291 (027 ribotype) and 630Δerm (012 ribotype), as active vegetative cell cultures. These two distinct strains were chosen because the genomes of both have been sequenced, and these strains are genotypically quite different from one another. The 630Δerm strain is the most commonly studied laboratory strain and is easier to manipulate genetically, while R20291 represents the current epidemic isolates. For comparison, three agents of known efficacy, the clinical antibiotic vancomycin, the lantibiotic nisin, and the human host-defense peptide LL-37 (McBride, S. M.; Sonenshein, A. L. *Microbiology* 2011, 157, 1457) were also evaluated. As shown in Table 1, each agent demonstrated similar efficacy against vegetative cell growth for the two *C. difficile* strains. The polymer MIC values were 12.5 to 25 μg/mL. These values are inferior to the MIC values of vancomycin, comparable to the MIC values of LL-37, and superior to the MIC values of nisin.

TABLE 1

Activity of Nylon-3 Polymers and Antimicrobial Peptides toward *C. difficile* Vegetative Cells and Spores.

| | R20291 | | 630Δerm | |
|---|---|---|---|---|
| antimicrobial | MIC[a] | OIC[b] | MIC[a] | OIC[b] |
| 50:50 MM:CH | 25 | 6.25 | 25 | 12.5 |
| 50:50 DM:CH | 12.5 | 6.25 | 12.5 | 12.5 |
| 50:50 DM:TM | 12.5 | 3.13 | 12.5 | 6.25 |
| LL-37 | 10 | 5 | 10 | 10 |
| nisin | 180 | 22.5 | 180 | >720[c] |
| vancomycin | 0.5 | 0.25 | 1 | >32[c] |

[a]The miminum inhibitory concentration for vegetative cell growth (MIC; μg/mL).
[b]The minimum inhibition concentration for spore outgrowth (OIC; μg/mL).
[c]Higher concentrations were not examined.

4. Nylon-3 Polymers Reduce *C. difficile* Spore Outgrowth

During infection, *C. difficile* is present in both the vegetative and spore forms. The transition from dormant spore to vegetative bacillus is initiated by the germinant taurocholate, a bile salt found within the intestine. Once initiated, germination progresses in a pre-programmed manner that does not require active cellular metabolism. (See Setlow, P. *Curr. Opin. Microbiol.* 2003, 6, 550; Setlow, P. *J. Appl. Microbiol.* 2013, 115, 1251; Paredes-Sabja, D.; Shen, A.; Sorg, J. A. *Trends Microbiol.* 2014, 22, 406; and Paredes-Sabja, D.; Setlow, P.; Sarker, M. R. *Trends Microbiol* 2011, 19, 85.) This transition is followed by an outgrowth phase in which metabolic processes are re-established, the cell is remodeled, and vegetative growth resumes. (Moir, A. *J. Appl. Microbiol.* 2006, 101, 526.) During the outgrowth phase the transitioning cell has only a limited ability to adapt to stress, creating a window of vulnerability to environmental conditions. It was discovered by the present co-inventors the nylon-3 polymers can influence spore survival, germination, or the subsequent outgrowth into vegetative cells.

To test whether polymers inhibit the outgrowth of spores into vegetative cells, the MIC experiments were replicated using spores as inoculum and supplementing with 0.1% taurocholate to stimulate germination of the spores. It should be noted that this experiment does not specifically measure sporicidal activity. Table 1 summarizes the results, as manifested by outgrowth inhibitory concentration (OIC). The nylon-3 polymers displayed OIC values in the range 3.13 to 12.5 μg/mL, indicating that these materials are comparable to or slightly more effective at preventing the outgrowth of spores relative to their inhibition of vegetative cell growth. That is, the observed OIC values are comparable to or slightly lower than the corresponding MIC values. In addition, each polymer and each of the comparison compounds was more effective at blocking outgrowth of the clinically important 027 epidemic spores (R20291 strain) than at blocking outgrowth of the non-epidemic 630 strain. This strain-dependent variation was small for the polymers and LL-37, but large for nisin and vancomycin. Neither and vancomycin displayed no inhibition of spore outgrowth for the 630 strain. These observations suggest that strain-dependent differences in spore composition and/or outgrowth characteristics can significantly affect susceptibility to inhibition of outgrowth by conventional antibiotics but not by LL-37 or the nylon-3 polymers. In addition, the contrast between low MIC values but high OIC values for nisin and vancomycin toward the 630 strain shows that the inhibition of spore outgrowth differs in some fundamental way from inhibition of vegetative cell growth.

5. Antimicrobial Polymers Inhibit Spore Outgrowth but Not Germination

The inhibitory effects documented in Table 1 could arise in at least three different ways: (1) destruction of spore viability; (2) prevention of germination; or (3) inhibition of growth of cells transitioning from the spore to the vegetative form. In order to gain insight on the putative mechanism(s) of action, experiments were conducted to determine whether germination is inhibited by the polymers or reference compounds. Spores were incubated with each agent at concentrations above the OIC for 24 h in the absence of germinant. Spores were then diluted and plated onto BHIS agar medium containing the germinant taurocholate. The preincubation resulted in moderate decreases in colony-forming units (CFU) for all agents tested (4-fold or less; data not shown). As shown by the microscopy data in FIGS. 1A and 1B, pre-incubation of spores with the polymers or reference compounds followed by the addition of germinant resulted in no change in the rates of spore germination for either *C. difficile* strain (transition from phase bright to phase dark spores). These results indicate that nylon-3 polymers and the reference compounds do not destroy spores or directly block germination, but instead they target the germinated spores. Spores are highly resistant to environmental insults. But as a spore converts into a vegetative cell during the outgrowth phase, the cell surface is completely remodeled. At the same time, there are drastic changes in gene expression necessary for growth. As a result, the spore-outgrowth period represents a point of vulnerability to antimicrobial agents, as manifested in these observations. See McBride, S. M.; Sonenshein, A. L. *Microbiology* 2011, 157, 1457 and Fisher, N., et al. *J. Bacteriol.* 2006, 188, 1301.

6. Evidence of Variation in Germination Propensity among Spores.

Experiments were conducted to determine whether any spores fail to germinate under the conditions of the OIC measurement but remain viable for subsequent germination and outgrowth. Spores were incubated for 24 h in the presence of germinant (taurocholate) and one of the polymers or other agents at multiple concentrations above the OIC. These solutions were then diluted 10 to 100-fold into sterile PBS, and further diluted upon plating onto BHIS agar medium containing germinant to achieve concentrations below the OIC of the relevant antimicrobial agent. Spore survival was calculated as the percentage of colony-forming units retrieved on outgrowth plates relative to the initial spore inoculum (100%). These studies were conducted with both strains of *C. difficile*; however, neither vancomycin nor nisin was assessed with strain 630, since these compounds did not inhibit spore outgrowth for this strain (Table 1).

The data from these experiments reveal that a small proportion of the original spores, typically in the range 0.5 to 3%, remain in a viable form in samples for which no spore outgrowth activity could be detected in the OIC analysis (see Table 2). Within the limits of experimental uncertainty, this residual proportion of germination-competent spores did not change as the concentration of each nylon-3 polymer or other antibacterial agent was increased above the OIC. The small subpopulation of germination-competent spores detected via these experiments presumably reflects an intrinsic heterogeneity within any sample of *C. difficile* spores. It is possible that the community derives a selective advantage if a small set of spores fails to undergo germination upon a given exposure to favorable conditions but nevertheless remains competent for germination at a subsequent time. Such a germination-resistant population might be functionally comparable to the small population of slow-growing "persister cells" that are proposed to occur within bacterial populations and underlie the development of antibiotic resistance. (Balaban, N. Q.; Gerdes, K.; Lewis, K.; McKinney, J. D. *Nat. Rev. Microbiol.* 2013, 11, 587.) If this hypothesis regarding the nature of the germination-resistant spores is correct, then the nylon-3 polymers might have an advantage in vivo relative to HDPs such as LL-37 in blocking *C. difficile* growth: peptides are inherently susceptible to protease-mediated destruction, but previous studies with discrete β-peptide oligomers suggest that the nylon-3 polymers are not substrates for proteases. (Frackenpohl, J.; Arvidsson, P. I.; Schreiber, J. V.; Seebach, D. *ChemBioChem* 2001, 2, 445.) Thus, the subject nylon-3 polymers should retain their ability to inhibit outgrowth of slow-germinators over long periods in vivo, while a peptide would be rapidly inactivated.

TABLE 2

Viability of Spores Recovered from Outgrowth Inhibition (OIC) Assays.

| Compound | Concentration (μg/ml) | R20291 Mean Spore Viability | 630ΔErm Mean Spore Viability |
|---|---|---|---|
| 50:50 DM:TM | 200 | 0.5% (±0.1%) | 1.4% (±0.5%) |
| | 100 | 0.4% (±0.2%) | 0.7% (±0.2%) |
| | 50 | 0.4% (±<0.1%) | 0.5% (±0.1%) |
| | 25 | 0.3% (±0.1%) | 0.7% (±0.3%) |
| | 12.5 | 0.4% (±<0.1%) | 1.1% (±0.7%) |
| 50:50 DM:CH | 200 | 1.8% (±0.8%) | 4.7% (±1.7%) |
| | 100 | 1.0% (±0.6%) | 3.1% (±0.9%) |
| | 50 | 0.4% (±<0.1%) | 3.5% (±2.3%) |
| | 25 | 0.5% (±0.1%) | 2.5% (±1.7%) |
| | 12.5 | 0.9% (±0.2%) | ND |

TABLE 2-continued

Viability of Spores Recovered from Outgrowth Inhibition (OIC) Assays.

| Compound | Concentration (μg/ml) | R20291 Mean Spore Viability | 630ΔErm Mean Spore Viability |
|---|---|---|---|
| 50:50 MM:CH | 200 | 0.5% (±0.1%) | 2.7% (±2.0%) |
| | 100 | 0.6% (±0.2%) | 1.4% (±0.5%) |
| | 50 | 0.5% (±0.1%) | 1.5% (±0.5%) |
| | 25 | 0.7% (±0.2%) | 6.0% (±5.2%) |
| | 12.5 | 2.9% (±3.6%) | ND |
| LL-37 | 80 | 5.8% (±2.9%) | 7.8% (±3.9%) |
| | 40 | 3.6% (±1.8%) | 4.0% (±4.0%) |
| | 20 | 1.2% (±0.7%) | 5.5% (±7.4%) |
| | 10 | 0.4% (±0.7%) | ND |
| Nisin | 360 | 0.4% (±<0.1%) | NI |
| | 180 | 0.2% (±0.2%) | NI |
| | 90 | 0.4% (±<0.1%) | NI |
| Vancomycin | 8 | 0.9% (±0.2%) | NI |
| | 4 | 1.3% (±0.2%) | NI |
| | 2 | 3.4% (±2.4%) | NI |
| | 1 | 7.7% (±7.5%) | NI |
| | 0.5 | 21.1% (±21%) | NI |

NI = Not Inhibitory;
ND = Not Determined

7. Hemolytic Activities

Figure 2:
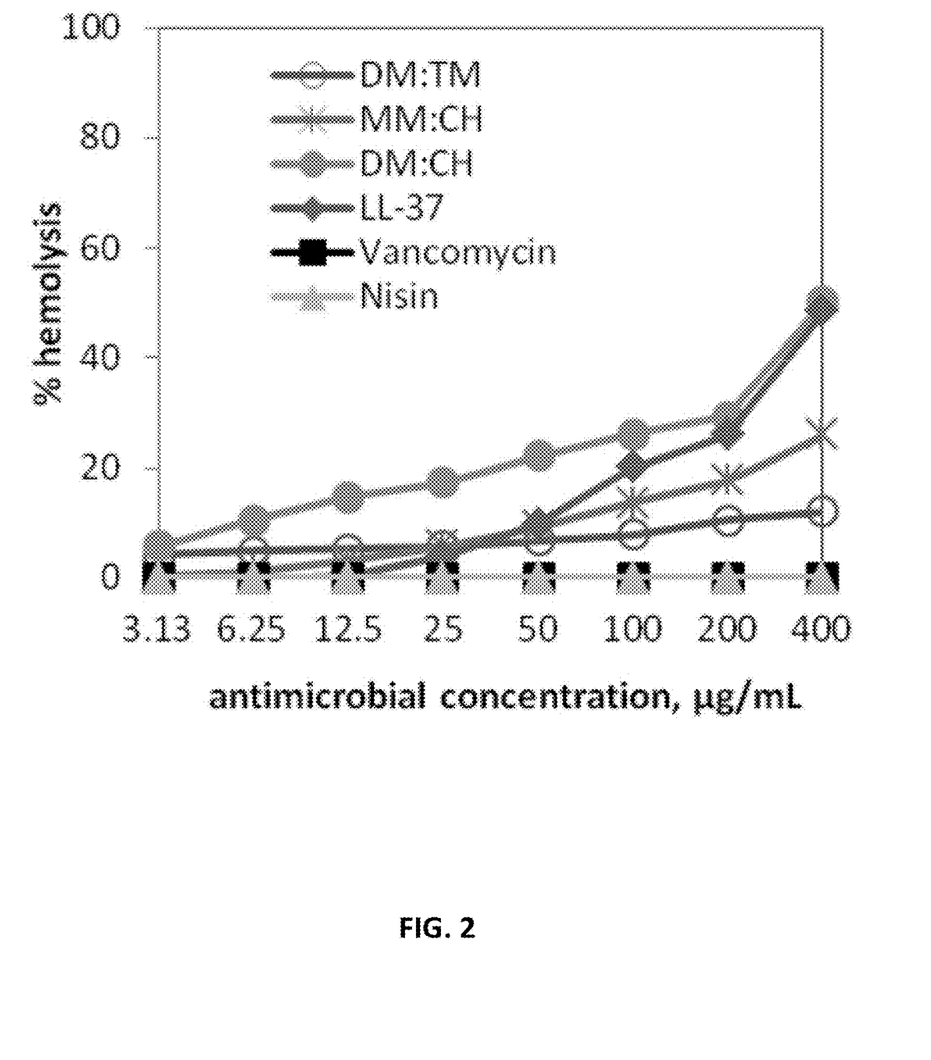
FIG. 2 is a graph depicting hemolytic profiles of selected nylon-3 polymers and antimicrobial compounds. Key: ○=DM:TM. *=MM:CH. ●=DM:CH. ◆=LL-37. ■=vancomycin. ▲=nisin.

HDPs and HDP-mimetic polymers are thought to exert antibacterial effects via disruption of membrane barrier function. Therefore, prokaryotic versus eukaryotic cell selectivity is often assessed by determining whether an agent that exerts antibacterial activity also causes disruption of human red blood cell (hRBC) membranes ("hemolysis"). As shown in FIG. 2, the three nylon-3 copolymers and the three comparison compounds display varied hemolytic activities. The data for the polymers are consistent with previously reported results. (Liu, R. et al. *J. Am. Chem. Soc.* 2014, 136, 4410.) Host-defense peptide LL-37 and polymer 50:50 DM:CH both display significant hemolytic activity. In contrast, 50:50 DM:TM causes very little hemolysis at the MIC/OIC and only mild hemolysis at high concentrations (400 μg/mL). Thus, 50:50 DM:TM manifests the most favorable activity profile among the materials evaluated to date. The 50:50 DM:TM polymer is both nonhemolytic and is quite active against both *C. difficile* strains in terms of inhibiting vegetative cell growth and spore outgrowth.

8. Discussion

*C. difficile* infections are often recurrent, and few effective antimicrobial treatment options are available. Because *C. difficile* spores are not inactivated by standard drugs or common disinfectants, patients may become re-infected by endogenous spores or spores lingering in their environment. As a result, clinical symptoms of CDI frequently return when antibiotic therapy is discontinued. With so few effective options for the treatment of CDIs and antimicrobial resistance pressure from frequent use of conventional antibiotics such as vancomycin, there is an urgent need for additional treatment strategies to combat infections by this pathogen. See Vonberg, R. P., et al. *Clin. Microbiol. Infect.* 2008, 14 (Suppl 5), 2.; Gerding, D. N., et al. *Infect. Control Hosp. Epidemiol.* 1995, 16, 459; Zar, F. A., et al. *Clin. Infect. Dis.* 2007, 45, 302; Petrella, L. A., et al. *Clin. Infect. Dis.* 2012, 55, 351; and Musher, D. M., et al. *J. Clin. Infect. Dis.* 2005, 40, 1586.

Some nylon-3 polymers were previously shown to be active against other pathogenic bacteria including methicillin-resistant *Staphylococcus aureus* (MRSA), vancomycin-resistant *Enterococcus faecium* (VREF), *Salmonella enterica* LT2, *Bacillus cereus* ATCC14579, *Pseudomonas aeruginosa* PA1066, and the uropathogenic *E. coli* CFT073. Liu, R., et al. *J. Am. Chem. Soc.* 2014, 136, 4410. None of these bacteria, however, are obligate anaerobes, as is *C. difficile*. The initial survey identified three hydrophobic/cationic copolymers that are particularly effective at preventing *C. difficile* growth: 50:50 DM:TM, 50:50 DM:CH, and 50:50 MM:CH. These polymers inhibit growth of the vegetative form of the pathogen, and they prevent outgrowth of the spore form of *C. difficile*. Preventing growth of vegetative cells is key to controlling infection and preventing the production of toxins that lead to human disease. Preventing the outgrowth of spores has the added advantage of avoiding vegetative growth entirely. It should be noted that inhibition of spore outgrowth is a distinct activity relative to inhibition of vegetative cell growth, as indicated by differences between MIC and OIC for nisin and vancomycin. See Table 1. The disparity between these parameters for vancomycin with the 630 strain is particularly striking. The combined effect of blocking spore outgrowth and inhibiting vegetative cell growth leads to fewer bacterial cells capable of becoming spores, thereby decreasing transmission of disease. Antimicrobial compounds such as nisin, oritavancin, fidaxomicin, and vancomycin are known to block the outgrowth of *C. difficile* endospores into vegetative cells. Chilton, C. H., et al. *J. Antimicrob. Chemother.* 2013, 68, 2078; Scott, V. N.; Taylor, S. L. *J. Food Sci.* 1981, 46, 117; Allen, C. A., et al. *Antimicrob. Agents Chemother.* 2013, 57, 664; and Gut, I. M., et al. *Antimicrob. Agents Chemother.* 2008, 52, 4281. However, the data presented here indicate that there is considerable strain-dependent variability in the effectiveness of nisin and vancomycin at preventing spore outgrowth. For clinical applications, it is best (although not required) if an agent can prevent both vegetative cell growth and spore outgrowth for multiple strains because these two modes of action are synergistic in terms of lessening the potential for virulence by reducing the number of cells capable of producing toxins A and B.

Each nylon-3 polymer inhibits spore outgrowth for both strains of *C. difficile* (Table 1). The HDP LL-37 shows comparable activity, but the antibiotics vancomycin and nisin vary considerably between the R20291 and 630 strains in terms of spore outgrowth inhibition. These comparisons support the view that the nylon-3 copolymers are functional mimics of HDPs. Comparisons of hemolytic activities (FIG. 2) show that a nylon-3 copolymer (specifically, 50:50 DM:TM) can be superior to a human HDP (LL-37) in terms of avoiding this undesirable property.

It was surprising to discover that nisin and vancomycin manifest disparate effects on spore outgrowth for different strains of *C. difficile*. Nisin has been shown to kill vegetative *C. difficile* and to inhibit the spore outgrowth of other species, such as *Bacillus anthracis* and *Clostridium botulinum*. Some strains of *C. botulinum* exhibit higher spore resistance to nisin than others, which parallels the current observations regarding nisin effects on different strains of *C. difficile*. *C. botulinum* spores are more resistant than vegetative cells to nisin. Mazzotta, A. S.; Crandall, A. D.; Montville, T. *J. Appl. Environ. Microbiol.* 1997, 63, 2654. *C. difficile* has mechanisms to resist killing by nisin, and spontaneous mutations that confer high nisin resistance have been described. See Suarez, J. M.; Edwards, A. N.; McBride, S. M. *J. Bacteriol.* 2013, 195, 2621. Together, these factors limit the therapeutic potential of nisin and similar compounds for treatment of CDIs.

Vancomycin was previously found to prevent spore outgrowth for 027 epidemic isolates of *C. difficile* (Allen, C. A.; Babakhani, F.; Sears, P.; Nguyen, L.; Sorg, J. A. *Antimicrob. Agents Chemother.* 2013, 57, 664), and the current findings are consistent with this precedent. However, vancomycin is completely ineffective at inhibiting outgrowth of the 012 ribotype spores. This observation is striking given the low MIC measured for vancomycin against vegetative cells for the 012 ribotype. One possible explanation of these findings is that vancomycin is sequestered by 012 (strain 630) spores, which allows the cells that germinate to survive and grow in levels of vancomycin that far exceed the MIC. Because spores are always present during infections, this hypothesis could explain the failure of vancomycin treatment for some CDIs and the relapse of infections. (Mazzotta, A. S.; Crandall, A. D.; Montville, T. *J. Appl. Environ. Microbiol.* 1997, 63, 2654.) Further studies are needed to determine how the efficacies of vancomycin and other antimicrobial agents are affected by the presence of spores from different strains of *C. difficile*. The proposed capacity of spores to sequester certain antimicrobial agents could be an important consideration in the selection of therapeutic strategies. Altogether, the data support that nylon-3 copolymers are effective active agents to combat CDIs. The facile synthesis and ease of compositional variation of nylon-3 materials make this class of synthetic polymers attractive for clinical applications.

9. Pharmaceutical Compositions and Methods:

Also disclosed herein are pharmaceutical compositions comprising one or more of the nylon-3 polymers or a pharmaceutically suitable salt thereof as described herein. The compositions are used to treat, inhibit, or otherwise ameliorate *C. difficile* infections and re-infections in mammals, including human beings. More specifically, the pharmaceutical composition may comprise one or more of the nylon-3 polymers as well as a standard, well-known, nontoxic pharmaceutically suitable carrier, adjuvant or vehicle such as, for example, phosphate buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectible, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active compound(s), may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, nylon-3 polymers produced as described herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant nylon-3 polymer(s). For intravenous administration, the nylon-3 polymers may be incorporated into commercial formulations such as Intralipid©-brand fat emulsions for intravenous injection. ("Intralipid" is a registered trademark of Fresenius Kabi AB, Uppsalla, Sweden.) Where desired, the individual components of the formulations may be provided individually, in kit form, for single or multiple use. A typical intravenous dosage of a representative nylon-3 polymer as described herein is from about 0.1 mg to 100 mg daily and is preferably from 0.5 mg to 3.0 mg daily. Dosages above and below these stated ranges are specifically within the scope of the claims.

Possible routes of administration of the pharmaceutical compositions include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant. The route of administration will, of course, depend upon the desired effect and the medical stated of the subject being treated. The dosage of the composition to be administered to the patient or subject may be determined by one of ordinary skill in the art and depends upon various factors such as weight of the patient, age of the patient, immune status of the patient, etc., and is ultimately at the discretion of the medical professional administering the treatment. Veterinary use is also within the scope of the method, and thus the species of the subject being treated would also be taken into account.

With respect to form, the composition may be, for example, a solution, a dispersion, a suspension, an emulsion or a sterile powder which is then reconstituted. The composition may be administered in a single daily dose or multiple doses.

The present disclosure also includes treating, inhibiting, and/or otherwise amelioriating *C. difficile* infections and re-infections in mammals, including humans, by administering a *C. difficile* spore outgrowth inhibitory-effective amount of, or a *C. difficile* vegetative cell growth inhibitory-effective amount of, one or more nylon-3 polymers. In particular, the compositions may be used to treat *C. difficile* infections of any and all description, at any growth stage of the *C. difficile* organism.

It should be noted that the above-described pharmaceutical compositions may be utilized in connection with non-human animals, both domestic and non-domestic, as well as humans.

EXAMPLES

The following examples are included solely to provide a more complete disclosure of the compounds, compositions, and methods described and claimed herein. The examples do not limit the scope of the claims in any fashion.

Bacterial Strains and Growth Conditions. Genotypically distinct *C. difficile* strains 630Δerm (ribotype 012) and R20291 (epidemic, ribotype 027) were obtained from Nigel Minton and Linc Sonenshein, respectively, and used in this study. See Hussain, H. A.; Roberts, A. P.; Mullany, P. *J. Med. Microbiol.* 2005, 54, 137; Wust, J.; Hardegger, U. *Antimicrob. Agents Chemother.* 1983, 23, 784; and Stabler, R. A.; He, M.; Dawson, L.; Martin, M.; Valiente, E.; Corton, C.; Lawley, T. D.; Sebaihia, M.; Quail, M. A.; Rose, G.; Gerding, D. N.; Gibert, M.; Popoff, M. R.; Parkhill, J.; Dougan, G.; Wren, B. W. *Genome Biol.* 2009, 10, R102. *C. difficile* strains were cultured in an anaerobic chamber maintained at 37° C. (Coy Laboratory Products, Grass Lake, Mich.) with an atmosphere of 10% $H_2$, 5% $CO_2$, and 85% $N_2$ as previously described. (Bouillaut, L.; McBride, S. M.; Sorg, J. A. Genetic Manipulation of *Clostridium difficile*.

Current Protocols in Microbiology; John Wiley & Sons, Inc.: New York, 2011; Chapter 9, Unit 9A.2; Edwards, A. N.; Suarez, J. M.; McBride, S. M. *J. Visualized Exp.* 2013, DOI: 10.3791/50787.) Taurocholate was added to cultures (0.1%) to induce germination of *C. difficile* spores as indicated (Sigma-Aldrich, St. Louis, Mo.). (Sorg, J. A.; Dineen, S. S. Laboratory Maintenance of *Clostridium difficile. Current Protocols in Microbiology*; John Wiley & Sons, Inc.: New York, 2009; Chapter 9, Unit 9A.1; Putnam, E. E.; Nock, A. M.; Lawley, T. D.; Shen, A. *J. Bacteriol.* 2013, 195, 1214.) Cells were routinely cultured on brain-heart infusion medium supplemented with 0.5% yeast extract and 1.5% agar (BHIS, BD Difco, Franklin Lakes, N.J.). (Smith, C. J.; Markowitz, S. M.; Macrina, F. L. *Antimicrob. Agents Chemother.* 1981, 19, 997.) All experiments were performed using prereduced Mueller-Hinton (MH) broth (BD Difco) unless otherwise specified.

Synthesis and Characterization of Nylon-3 Polymers. All nylon-3 polymers used in this study were synthesized in a moisture-controlled glove box using either tetrahydrofuran (THF) for MM- and DM-containing polymers or dimethylacetamide (DMAc) for NM-containing polymers as the reaction solvent as previously described. See Liu, R. H.; Chen, X. Y.; Gellman, S. H.; Masters, K. S. *J. Am. Chem. Soc.* 2013, 135, 16296 and also U.S. Pat. No. 8,519,095 to Stahl et al. Briefly, a mixture of β-lactam monomers and the co-initiator (tertbutylbenzoyl chloride) in a 10 mL glass vial was dissolved in THF (or DMAc), followed by the addition of co-initiator solution in THF (or DMAc). The mixture was mixed under magnetic stirring and treated with a solution of lithium bis(trimethylsilyl)amide in THF. The reaction mixture was stirred overnight at room temperature and then removed from the glove box and quenched with a few drops of methanol. The reaction mixture was poured into a centrifuge tube containing pentane to precipitate the side-chain-protected polymer as white solid. Protected polymers were dried with $N_2$ and then subjected to gel permeation chromatography (GPC) characterization using THF or DMAc as the mobile phase. GPC results are shown in Table 3. Protected polymers were treated with trifluoroacetic acid (TFA) at room temperature for 2 h to remove the Boc groups from side chain amines. Deprotected polymers were precipitated in diethyl ether and collected after centrifugation and drying with $N_2$ to provide TFA salts as white solids. Side-chain protected NM-containing polymers were characterized by GPC using DMAc as the mobile phase as described previously. Liu, R. H.; Chen, X. Y.; Hayouka, Z.; Chakraborty, S.; Falk, S. P.; Weisblum, B.; Masters, K. S.; Gellman, S. H. *J. Am. Chem. Soc.* 2013, 135, 5270. The DMAc gel permeation chromatograph (Waters Corporation, Millford, Mass.) was equipped with two Waters Styragel HR 4E columns (5 μm particle) linked in series and a refractive index detector (Waters 2410). DMAc (supplemented with 10 μM LiBr) was used as the mobile phase at a flow rate of 1 mL/min at 80° C. Side-chain-protected MM- and DM-containing polymers were characterized by GPC using THF as the mobile phase as described previously. Id. The THF gel permeation chromatograph (Shimadzu N.A., Columbia, Md.) was equipped with two Waters columns (Styragel HR 4E, particle size 5 μm) linked in series, a multi-angle light scattering detector (Wyatt miniDAWN, 690 nm, 30 mW, Wyatt Technology Corporation, Santa Barbara, Calif.), and a refractive index detector (Wyatt Optilab-rEX, 690 nm). THF was used as the mobile phase at a flow rate of 1 mL/min at 40° C. $^1H$ spectra were collected on a Bruker Avance III 400 spectrometer at 100 MHz using $D_2O$ as the solvent (Bruker Corporation, Billerica, Mass.). $^1H$ NMR chemical shifts were referenced to the resonance for residual protonated solvent (δ 4.79 for $D_2O$). MM-TM polymers were characterized by GPC at the side-chain NHBOc-protected stage using do/dc of 0.1 ml/g for all polymers as described previously. Id. The fully deprotected MM-TM polymers were characterized by $^1H$ NMR (data not shown). All other polymers were reported and characterized previously. (Liu, R. H.; Chen, X. Y.; Hayouka, Z.; Chakraborty, S.; Falk, S. P.; Weisblum, B.; Masters, K. S.; Gellman, S. H. *J. Am. Chem. Soc.* 2013, 135, 5270; Liu, R.; Chen, X.; Falk, S. P.; Mowery, B. P.; Karlsson, A. J.; Weisblum, B.; Palecek, S. P.; Masters, K. S.; Gellman, S. H. *J. Am. Chem. Soc.* 2014, 136, 4333; and Liu, R.; Chen, X.; Chakraborty, S.; Lemke, J. J.; Hayouka, Z.; Chow, C.; Welch, R. A.; Weisblum, B.; Masters, K. S.; Gellman, S. H. *J. Am. Chem. Soc.* 2014, 136, 4410.)

TABLE 3

GPC Characterization of Nylon-3 Copolymers.

| polymer | expected subunit ratio (cationic:hydrophobic) | expected Mn | GPC characterization[a] | | | NMR characterization[b] | observed subunit ratio (cationic:hydrophobic) |
|---|---|---|---|---|---|---|---|
| | | | $PDI_{GPC}$ | $Mn_{GPC}$ | $DP_{GPC}$ | $DP_{NMR}$ | |
| 40:60 NM:TM | 40:60 | 3399 | 1.22 | 2338 | 14 | 12 | 68:32 |
| 50:50 MM:TM | 50:50 | 3574 | 1.16 | 2825 | 17 | 13 | 76:24 |
| 60:40 MM:TM | 60:40 | 3748 | 1.15 | 3274 | 18 | 14 | 83:17 |
| 70:30 MM:TM | 70:30 | 3922 | 1.17 | 3423 | 18 | 15 | 85:15 |
| 80:20 NM:TM | 80:20 | 4096 | 1.15 | 3774 | 19 | 16 | 88:12 |
| 90:10 MM:TM | 90:10 | 4270 | 1.13 | 4370 | 21 | 18 | 92:8 |
| 50:50 MM:CH | 50:50 | 3555 | 1.32 | 4938 | 28 | 24 | 46:54 |
| 50:50 DM:CH | 50:50 | 3694 | 1.05 | 4766 | 26 | 26 | 50:50 |

TABLE 3-continued

GPC Characterization of Nylon-3 Copolymers.

| polymer | expected subunit ratio (cationic:hydrophobic) | expected Mn | GPC characterization[a] | | | NMR characterization[b] | observed subunit ratio (cationic:hydrophobic) |
|---|---|---|---|---|---|---|---|
| | | | PDI$_{GPC}$ | Mn$_{GPC}$ | DP$_{GPC}$ | DP$_{NMR}$ | |
| 50:50 DM:TM | 50:50 | 3714 | 1.13 | 3205 | 18 | 17 | 60:40 |

[a]PDI is the polydispersity index; Mn is the number average molecular weight at the side chain protected stage; DP is the degree of polymerization, i.e., the average number of subunits, calculated from GPC characterization of side chain protected (NHBoc) polymers using THF as the mobile phase.
[b]DP and subunit ratio were calculated independently from NMR data using the integration of proton signals.
Aromatic protons of N-terminal t-BuBz group were used for calibration and subunit ratio calculation.
Polymers 50:50 MM:CH, 50:50 DM:CH and 50:50 DM:TM were reported previously (Liu, R., et al. *J. Am. Chem. Soc.* 2014, 136, 4333; and Liu, R., et al. *J. Am. Chem. Soc.* 2014, 136, 4410); the data are included here for comparison with the MM:TM series polymers.

Hemolysis Assays. Hemolysis assays were conducted as previously described using human red blood cells (hRBCs). Raguse, T. L.; Porter, E. A.; Weisblum, B.; Gellman, S. H. *J. Am. Chem. Soc.* 2002, 124, 12774. hRBCs were obtained from the University of Wisconsin (Madison, Wis.) hospital blood bank, washed three times with TRIS-buffered saline (TBS; 10 mM TRIS, 150 mM NaCl, pH 7.2), and diluted 1:50 in TBS to provide a working suspension of 2% RBC relative to total RBC in whole blood. Two-fold serial dilutions of nylon-3 polymers were prepared in a 96-well plate using TBS; each well contained 100 μL of each compound in solution at concentrations ranging from 800 to 6.25 μg/mL. An aliquot of 100 μL of RBC working suspension was added to each well, followed by gentle shaking of the plate for 10 s. Wells containing TBS without polymer (blank) and wells containing Triton X-100 (positive control to give 100% hemolysis, 3.2 μg/mL in TBS) were included on the same plate. The plate was incubated at 37° C. for 1 h and then centrifuged at 3700 rpm for 5 min. An aliquot of 80 μL of the supernatant from each well was transferred to the corresponding well in a new 96-well plate, and the optical density (OD) at 405 nm was measured using a Molecular Devices Emax precision microplate reader (Molecular Devices, LLC, Sunnyvale, Calif.). Measurements were performed in duplicate, and each measurement was repeated on at least two different days. The percentage of hemolysis in each well of a representative data was calculated from $$\% \text{ hemolysis} = \frac{A_{405}^{polymer} - A_{405}^{blank}}{A_{405}^{control} - A_{405}^{blank}} \times 100$$

and plotted against polymer concentration to give the dose-response curves of hemolysis for these polymers.

Minimal Inhibitory Concentration (MIC) Determination. Antimicrobial susceptibility tests were performed anaerobically by microdilution in MH broth (BD Difco). (Mueller, J. H.; Hinton, *J. Proc. Soc. Exp. Biol. Med.* 1941, 48, 330; EUCAST. *Clin. Microbiol. Infect.* 2003, 9, ix.) To determine MICs, overnight cultures of *C. difficile* were diluted into 10 mL of MH broth and cultures grown to an OD$_{600}$=0.45 (~5×10$^7$ CFU/mL). Cultures were then diluted 1:10 in MH broth, and 15 μL samples of diluted cultures were used to inoculate individual wells of pre-reduced 96-well round-bottom polystyrene plates containing 135 μL of MH broth or MH broth containing antimicrobials to yield a starting concentration of ~5×10$^5$ CFU/mL. MH broth was supplemented with a range of concentrations (2-fold dilutions) of nisin (MP Biomedicals, MP Biomedicals, LLC, Santa Ana, Calif.), LL-37 (cathelicidin; AnaSpec, Inc., Fremont, Calif.), vancomycin (Sigma-Aldrich), or nylon-3 polymers, as specified. Each strain and antimicrobial agent concentration was tested in duplicate for each assay. Uninoculated medium was used as a negative control to test for contamination of growth medium. The positive control was inoculated with *C. difficile*, but no antimicrobial compound was added. The MIC was defined as the lowest concentration of drug in which no growth was observed after 24 h at 37° C., and the results of duplicate measurements were averaged. MIC assays were performed a minimum of three times to ensure reproducibility of results.

Spore Preparation and Quantification. *C. difficile* spores were prepared as described previously. (Edwards, A. N.; Nawrocki, K. L.; McBride, S. M. *Infect. Immun.* 2014, 82, 4276.) Briefly, strains were grown in BHIS broth overnight, spread onto 70:30 agar plates and incubated for 48 h to allow spores to form. (Putnam, E. E.; Nock, A. M.; Lawley, T. D.; Shen, A. *J. Bacteriol.* 2013, 195, 1214.) Following incubation, cells were scraped from the plates, washed in phosphate-buffered saline (PBS), and resuspended in 5 mL of PBS. Samples were then combined 1:1 with 95% ethanol and incubated at room temperature for 1 h to kill all vegetative cells. Spores were then pelleted, washed twice in PBS, and resuspended in 5 mL of fresh PBS. Spore suspensions were then heated to 70° C. for 20 min, followed by addition of PBS with 1% bovine serum albumin (BSA, Sigma-Aldrich) to prevent clumping. Spore preparations were serially diluted and plated onto BHIS agarcontaining 0.1% taurocholate to determine the number of spores present, and diluted prior to use. (Smith, C. J.; Markowitz, S. M.; Macrina, F. L. *Antimicrob. Agents Chemother.* 1981, 19, 997.)

Spore Inhibition and Vegetative Outgrowth Inhibitory Concentration (OIC) Assays. Because *C. difficile* spores can be killed prior to or during outgrowth to the vegetative form, multiple methods were used to assess the viability of *C. difficile* spores exposed to antimicrobials. First, the effect of antimicrobials on the outgrowth of spores (outgrowth inhibitory concentration; OIC) was determined as follows. Spore preparations were diluted to a final concentration of 5×10$^6$ CFU/mL, and 15 μL aliquots of spore preps were added to individual wells of pre-reduced 96-well plates containing 135 μL of MH broth and 0.01% taurocholate, with or without antimicrobials, to allow spore germination. MH broth was supplemented with dilutions of antimicrobials as described for MIC assays. The OIC was defined as the lowest concentration of drug in which no growth was observed after 24 h at 37° C. Assays were performed a minimum of three times to ensure reproducibility of results.

Immediately following OIC assays, samples were taken from wells in which no growth was observed to assess the viability and germination potential of spores exposed to concentrations of antimicrobials greater than or equal to the OIC values (i.e., spore outplating). Samples were diluted and plated onto BHIS medium containing 0.1% taurocholate and enumerated following incubation for at least 24 h at 37° C. Spore survival was calculated as the percentage of CFU post-assay/initial CFU.

To assess the effects of antimicrobials on spores prior to outgrowth, OIC assays were performed in the absence of germinant. Spores were incubated for 24 h at 37° C., followed by dilution and plating onto BHIS medium containing 0.1% taurocholate to enumerate spores that were inhibited or killed by antimicrobials. Spore survival was calculated as the percentage of CFU post-assay/initial CFU.

Phase-Contrast Microscopy of Spore Germination. *C. difficile* spores used for microscopy were purified as previously described with some modifications. (Sorg, J. A.; Sonenshein, A. L. *J. Bacteriol.* 2010, 192, 4983.) First, 70:30 agar medium was used for the preparation of spores from vegetative cells. Following spore removal from plates, a 48 h incubation step at −20° C. was added prior to layering the spore prep on top of a 50% sucrose gradient. Following washes with dH$_2$O, samples were washed three times in PBS containing 1% BSA to improve the dissociation of individual spores. Mature spores appear phase-bright under phase-contrast microscopy, while germinated spores appear phase-dark. Setlow, P. *J. Appl. Microbiol.* 2013, 115, 1251 and Moir, A.; Smith, D. A. *Annu. Rev. Microbiol,* 1990, 44, 531. *Journal of the American Chemical Society Article* 14504.

Figure 1A:
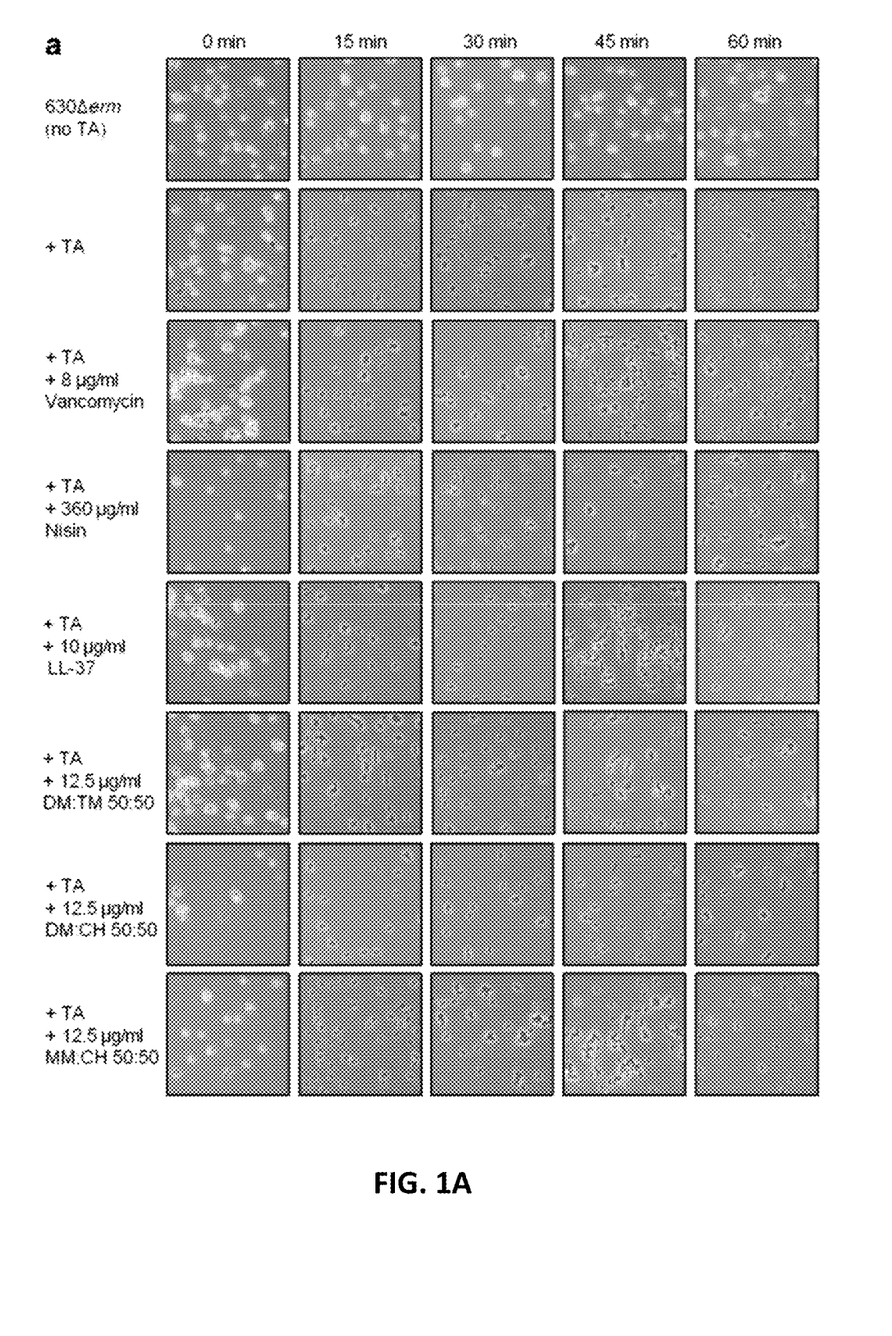
FIGS. 1A and 1B are phase-contrast photomicrographs of *C. difficile* spores incubated with antimicrobial compounds.
Figure 1B:
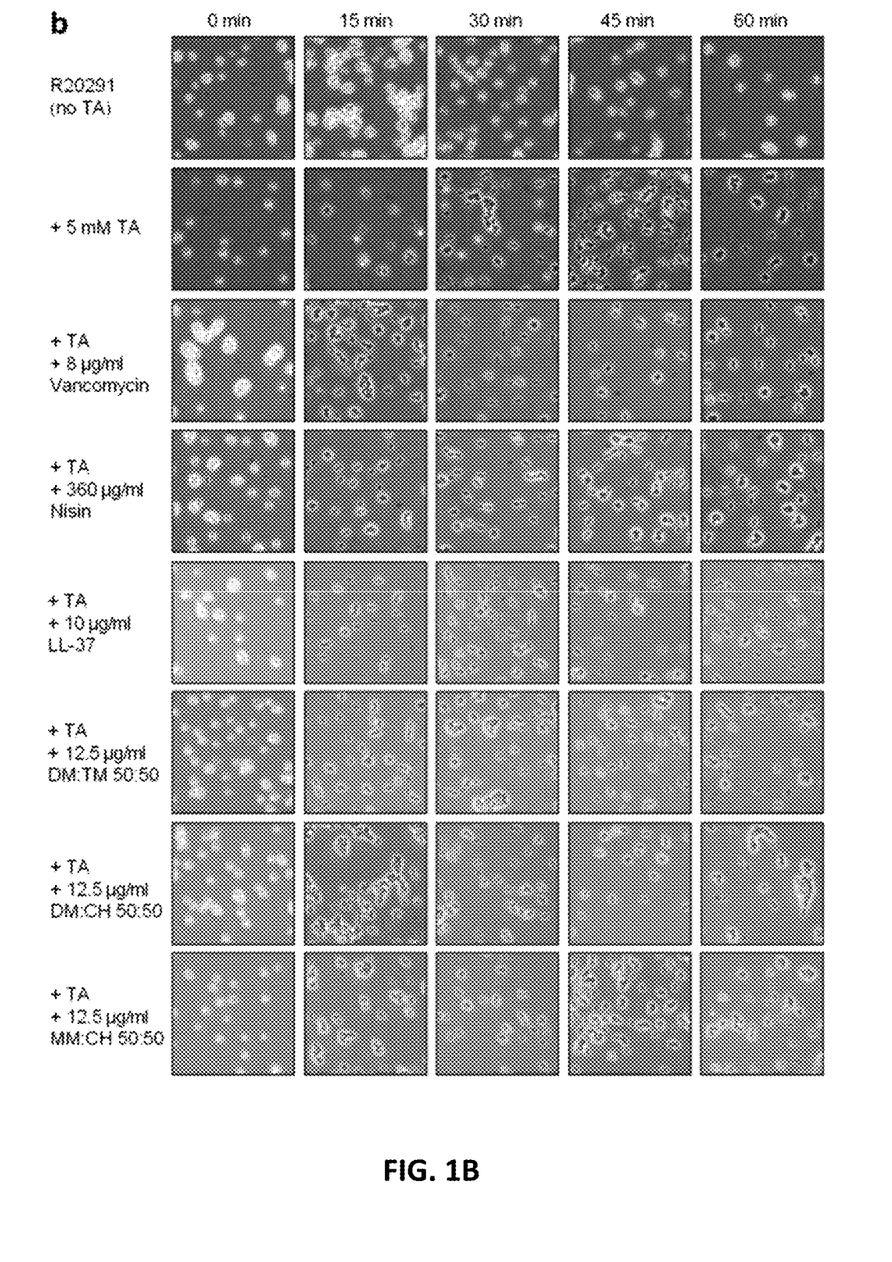

Prior to germination assessments, purified *C. difficile* spores were suspended in 100 µL of MH broth. Next, each of the tested compounds was added to the broth at the indicated final concentration and incubated at room temperature for 5 min. Taurocholate was then added to a final concentration of 5 mM, and samples were incubated at 37° C. for 1 h. Positive controls containing spores and taurocholate without antimicrobials and negative controls containing spores alone were performed in parallel. After the addition of taurocholate, 5 µL samples were harvested every 15 min and placed on a solidified 0.7% agarose surface layered on a microscope slide for visualization. Phase contrast microscopy was performed using a 100X-Ph3 oil immersion objective on a Nikon Eclipse $C_1$-L microscope, and images were acquired using an attached DS-Fi2 camera. Each strain and condition was tested a minimum of two times. At least three fields of view were acquired for each experimental condition. A representative image was shown in FIGS. 1A and 1B for each experimental condition tested.

What is claimed is:

1. A method of inhibiting outgrowth of *C. difficile* spores and/or inhibiting growth of *C. difficile* vegetative cells comprising contacting the spores or cells with an amount of a nylon-3 polymer or nylon-3 copolymer or a pharmaceutically suitable salt thereof, wherein the amount is effective to inhibit outgrowth of the *C. difficile* spores and/or to inhibit growth of the *C. difficile* vegetative cells.

2. The method of claim 1, wherein the nylon-3 polymer or copolymer comprises subunits selected from the group consisting of wherein:

$R^3$, $R^4$, $R^5$, and $R^6$ are each independently selected from the group consisting of hydrogen, substituted or unsubstituted $C_1$-$C_6$-alkyl, aryl, $C_1$-$C_6$-alklyaryl, amino, protected-amino, amino-$C_1$-$C_6$-alkyl, protected-amino-$C_1$-$C_6$-alkyl, guanidine, thioalkyl, alkylthioalkyl, amino-substituted alkylthioalkyl, or $R^3$ and $R^4$ combined define a cyclic substituent selected from the group consisting of $C_4$-$C_{12}$ cycloalkyl, $C_4$-$C_{12}$ cycloalkenyl, and five- to twelve-membered heterocyclic;

"n" is an integer from 0 to 8; and

"A" is selected from the group consisting of substituted or unsubstituted $C_4$-$C_{12}$ cycloalkyl, $C_4$-$C_{12}$ cycloalkenyl, and five- to twelve-membered heterocyclic.

3. The method of claim 1, wherein the nylon-3 polymer or copolymer has an average chain length of at least 5 subunits.

4. The method of claim 1, wherein the nylon-3 polymer or copolymer has an average chain length at of least 15 subunits.

5. The method of claim 1, wherein the nylon-3 polymer or copolymer has an average chain length at of at least 20 subunits.

6. The method of claim 1, wherein the nylon-3 polymer or copolymer has an average chain length at of between 5 and 120 subunits.

7. The method of claim 1, wherein the nylon-3 polymer or copolymer is selected from the group consisting of:

NM:CH, $x = 0.4$-$1$, $y = 1$-$x$

MM:TM, R = H DM:TM, R = Me $x = 0.4$-$1$, $y = 1$-$x$

50:50 MM:CH

50:50 DM:CH

50:50 DM:TM and wherein R is selected from the same group of substituents as $R^3$ through $R^6$.

8. A method of inhibiting outgrowth of C. *difficile* spores and/or inhibiting growth of C. *difficile* vegetative cells in a mammal comprising administering to the mammal an amount of a nylon-3 polymer or nylon-3 copolymer or a pharmaceutically suitable salt thereof, wherein the amount is effective to inhibit outgrowth of the C. *difficile* spores and/or to inhibit growth of the C. *difficile* vegetative cells in the mammal.

9. The method of claim 8, wherein the nylon-3 polymer or copolymer comprises subunits selected from the group consisting of and wherein:
$R^3$, $R^4$, $R^5$, and $R^6$ are each independently selected from the group consisting of hydrogen, substituted or unsubstituted $C_1$-$C_6$-alkyl, aryl, $C_1$-$C_6$-alklyaryl, amino, protected-amino, amino-$C_1$-$C_6$-alkyl, protected-amino-$C_1$-$C_6$-alkyl, guanidine, thioalkyl, alkylthioalkyl, amino-substituted alkylthioalkyl, or $R^3$ and $R^4$ combined define a cyclic substituent selected from the group consisting of $C_4$-$C_{12}$ cycloalkyl, $C_4$-$C_{12}$ cycloalkenyl, and five- to twelve-membered heterocyclic;

"n" is an integer from 0 to 8; and

"A" is selected from the group consisting of substituted or unsubstituted $C_4$-$C_{12}$ cycloalkyl, $C_4$-$C_{12}$ cycloalkenyl, and five- to twelve-membered heterocyclic.

10. The method of claim 8, wherein the nylon-3 polymer or copolymer has an average chain length at of at least 5 subunits.

11. The method of claim 8, wherein the nylon-3 polymer or copolymer has an average chain length at of at least 15 subunits.

12. The method of claim 8, wherein the nylon-3 polymer or copolymer has an average chain length at of at least 20 subunits.

13. The method of claim 8, wherein the nylon-3 polymer or copolymer has an average chain length at of between 5 and 120 subunits.

14. The method of claim 8, wherein the nylon-3 polymer or copolymer is selected from the group consisting of:

NM:CH, $x = 0.4\text{-}1$, $y = 1\text{-}x$

MM:TM, R = H DM:TM, R = Me  x = 0.4-1, y = 1-x

50:50 MM:CH

50:50 DM:CH

50:50 DM:TM wherein R is selected from the same group of substituents as $R^3$ through $R^6$.

15. The method of claim 8, wherein the amount of the nylon-3 polymer or copolymer is administered enterally.

16. The method of claim 8, wherein the amount of the nylon-3 polymer or copolymer is administered parenterally.

* * * * *